United States Patent [19]
Mueller, Jr.

[11] Patent Number: 4,577,637
[45] Date of Patent: Mar. 25, 1986

[54] FLEXIBLE METAL RADIOPAQUE INDICATOR AND PLUGS FOR CATHETERS

[75] Inventor: Richard L. Mueller, Jr., Athens, Tex.

[73] Assignee: Argon Medical Corp., Athens, Tex.

[21] Appl. No.: 630,570

[22] Filed: Jul. 13, 1984

[51] Int. Cl.⁴ ............................................. A61M 25/00
[52] U.S. Cl. ..................................... 128/658; 604/280
[58] Field of Search .............. 128/656, 657, 658, 772; 604/280, 285, 93, 264

[56] References Cited

U.S. PATENT DOCUMENTS

| | | | |
|---|---|---|---|
| 2,118,631 | 5/1938 | Wappler | 128/657 X |
| 3,906,938 | 9/1975 | Fleischhacker | 128/772 |
| 4,003,369 | 1/1977 | Heilman et al. | 128/772 |
| 4,020,829 | 5/1977 | Wilson et al. | 188/657 |

*Primary Examiner*—Stephen C. Pellegrino
*Attorney, Agent, or Firm*—Lawrence S. Levinson; Sanford J. Asman

[57] ABSTRACT

A combined radiopaque indicator and lumen plug for a multi-lumen catheter is made of a flexible, coiled metal spring having balled ends formed by resistance welding the ends of the coiled spring. The coiled spring plug is affixed within one or more lumens of a catheter to provide a radiopaque indicator.

5 Claims, 3 Drawing Figures

FLEXIBLE METAL RADIOPAQUE INDICATOR AND PLUGS FOR CATHETERS

BACKGROUND OF THE INVENTION

The present invention relates to catheter designs. In particular, it relates to a radiopaque indicator which may also be used as a plug in the lumen of a multi-lumen catheter.

Catheters are used in medical applications to introduce or extract fluids from the body. A variety of catheter designs have been used and are well known. Typically, catheters are flexible, plastic tubular structures having single or multiple openings called lumens. Many multiple lumen ("multi-lumen") catheters require plugging devices to terminate lumens at some opening along the catheter length.

The standard technology used for plugging lumens involves bonding a flexible plastic plug (using an adhesive or a solvent) into the lumen requiring the plug. The plastics used are normally soft, flexible, biomedically safe, radiopaque, and compatible with parent catheter materials. The limitation associated with using a plastic plugging material is principally one of radiopacity.

Radiopacity is important because it allows the physician to follow the catheter tip using a fluoroscope when the catheter is inserted into a patient. Accordingly, injury to the patient can be avoided. The degree of radiopacity of a plastic plug is determined by the amount of plastic filler, such as barium or bismuth, which the plastic contains. Typically, the filler concentration ranges from about 9% to about 24%. Although higher concentrations of radiopaque fillers are desirable, using existing technology, the filler percentage cannot be increased without losing the parent material's desirable properties, such as flexibility and strength.

Heretofore, metal radiopaque indicators, comprising solid metal bands formed around the exterior of a catheter, have been used. However, such exterior bands have the disadvantage of interrupting the smooth outer surface of the catheter as they may encourage thrombosis.

SUMMARY OF THE INVENTION

In accordance with the present invention a radiopaque indicator which may also be used as a plug for a lumen of a multi-lumen catheter is constructed from a finely coiled metal spring.

DETAILED DESCRIPTION OF THE PREFERRED EMBODIMENT

Figure 1:
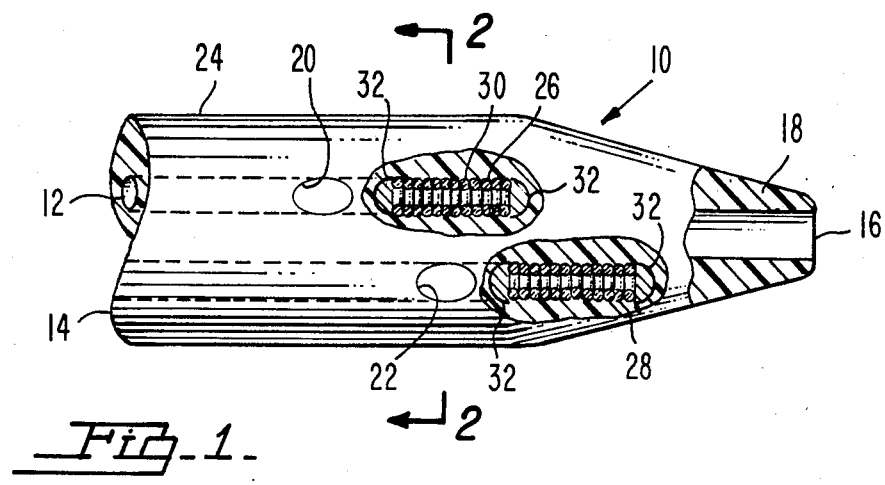
FIG. 1 is a side, partial cross-sectional view of a multi-lumen catheter using the present invention.

Referring generally to FIG. 1, a multi-lumen catheter 10 having three lumens 12, 14, 16 is shown. One of the lumens 16 extends through the end 18 of the catheter 10. The other lumens 12, 14 have openings 20, 22, respectively, through the wall 24 of the catheter 10.

Figure 2:
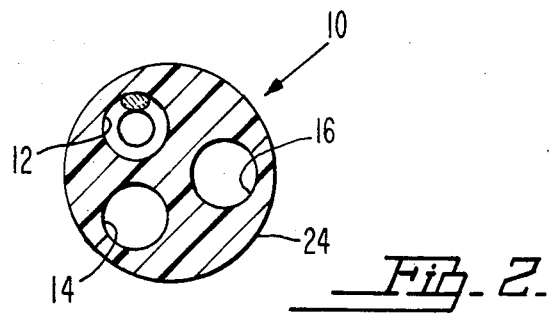
FIG. 2 is a cross-sectional view of the multi-lumen catheter taken along the lines 2—2 of FIG; 1.

In view of the fact that the catheter 10 is initially formed as a single extrusion, each of the lumens 12, 14, 16, initially extends along the entire length of the extrusion. Accordingly, in the course of manufacture, the end 18 of the catheter 10 is formed by inserting a wire (not shown) into each lumen which is to remain open to the end 18, i.e., the lumen 16 in the preferred embodiment shown in FIG. 2. The lumens which are to terminate before the end 18, i.e., the lumens 12, 14 in the catheter 10, are sealed at the end 18, and it is reformed by heating, which seals the ends of the lumens 12, 14. Side holes 20, 22 which are remote from the end 18, are formed to provide access to the terminated lumens 12, 14. The procedure just described would leave "dead end" portions of the lumens 12, 14 between the side holes 20, 22 and the end 18. As is well known, any blood which got into those "dead ends" could coagulate, resulting in problems. Accordingly, it is necessary to insert plugs between the side holes 20, 22 and the end 18 of the catheter 10 in the terminated lumens 12, 14.

Figure 3:
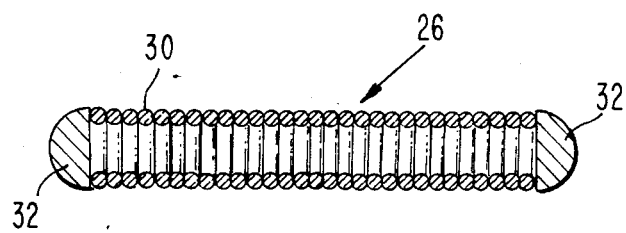
FIG. 3 is a cross-sectional view of the stainless steel spring plug of the preferred embodiment of the present invention.

In accordance with the present invention, lumen plugs 26, 28, respectively, comprised of coiled metal springs 30 having rounded ends 32 attached to either end of the coiled spring 30 (See FIG. 3) are used to plug the lumens 12, 14 before the end 18 is reformed. The lumens plugs 26, 28 are inserted into the lumens 12, 14 and are bonded just downstream of the side holes 20, 22. In the preferred embodiment of the invention, the springs are made of stainless steel. However, other radiopaque materials, such as platinum or gold, could also be used. In the preferred embodiment, the bonding is accomplished using a cyanoacrylate adhesive, such as Permabond which is manufactured by Permabond in Englewood, N.Y.

In order to manufacture the preferred embodiment of the invention, the rounded ends 32 are made by melting the ends of the coiled springs 30 to form them into hemispheres. This may be accomplished by a resistance welding process. The stainless steel plugs 26, 28 are extremely flexible. Accordingly, they do not restrict the flexibility of the catheter 10. The balled ends 32, when formed by resistance welding, will be fully radiused balls, i.e. as hemispheres, on either end of the spring 30 which serve to prevent the plugs 26, 26 from cutting through the side wall 24 of the catheter 10 and to seal the lumens 12, 14.

Advantages of the present invention are that the coiled metal plugs 30 can be made with variations in metal type, coil wire diameter, metal grade, and method of attachment. As will be obvious to those skilled in the art, while the present invention illustrates the use of the stainless steel coiled spring plug as both a lumen plug and as a radiopaque indicator, an unplugged coiled spring, in accordance with the invention, could also be used as a radiopaque indicator within a lumen which was intended to remain open without departing from the spirit or scope of the present invention. In such application, the coiled spring would still provide a superior radiopaque indicator, when compared to the prior plastic plugs, without affecting the flexibility of the catheter 10. By way of example, an open coiled spring plug could be used in a balloon catheter in which air is to be blown through the open coiled spring.

I claim:

1. An improved multi-lumen catheter of the type comprising at least two lumens which extend from a proximal end to a distal end thereof of the type requiring at least one plugging device to terminate at least one of said lumens, wherein the improvement comprises:

at least one radiopaque lumen plug comprised of a coiled metal spring having rounded end caps attached to either end of said coiled spring, said rounded end caps having an outside diameter substantially equal to the inside diameter of the lumen in which said plug is inserted, whereby said lumen will be blocked by said plug and said plug will act as a radiopaque indicator.

2. The multi-lumen catheter of claim 1 wherein said metal is selected from the group consisting of stainless steel, gold, and platinum.

3. The multi-lumen catheter of claim 2 wherein the individual coils of said coiled metal spring are closely spaced, so as to further prevent fluid flow therethrough.

4. The multi-lumen catheter of claim 3 wherein said end caps are formed as hemispheres.

5. The multi-lumen catheter of claim 4 wherein said end caps are made by resistance welding the ends of said spring.

* * * * *